United States Patent [19]

Stahl et al.

[11] 4,093,550
[45] June 6, 1978

[54] COLUMN FOR HIGH PRESSURE LIQUID CHROMATOGRAPHY

[75] Inventors: Kurt-Wilhelm Stahl, Hanover; Ekkehard Schuppe, Ronnenberg, both of Germany

[73] Assignee: Riedel-de Haen Aktiengesellschaft, Seelze, Germany

[21] Appl. No.: 691,531

[22] Filed: Jun. 1 1976

[30] Foreign Application Priority Data

Jun. 4, 1975 Germany ............................ 2524751

[51] Int. Cl.² .......................................... B01D 15/08
[52] U.S. Cl. ................................ 210/198 C; 210/287
[58] Field of Search ............... 210/31 C, 198 C, 120, 210/436; 55/67, 197, 386, 478, 418, 419

[56] References Cited

U.S. PATENT DOCUMENTS

| 2,823,804 | 2/1958 | Myring | 210/436 |
|---|---|---|---|
| 3,855,130 | 12/1974 | Randau | 210/198 C |

FOREIGN PATENT DOCUMENTS

| 1,525,794 | 7/1970 | Germany | 55/386 |
|---|---|---|---|
| 837,363 | 6/1960 | United Kingdom | 210/198 C |

Primary Examiner—John Adee
Attorney, Agent, or Firm—Connolly and Hutz

[57] ABSTRACT

In a column for high pressure liquid chromatography (HPLC) consisting of a glass column filled with sorbent concentrically surrounded by a pressure jacket leaving an interspace between the glass column and the pressure jacket, which interspace is sealed at both ends of the glass column and filled with the same medium as flows through the glass column, the pressure in the interspace being equal to the pressure at the inlet of the glass column, the improvement comprises packings surrounding the glass column like stuffing boxes and sealing the interspace between the glass column and the pressure jacket.

4 Claims, 1 Drawing Figure

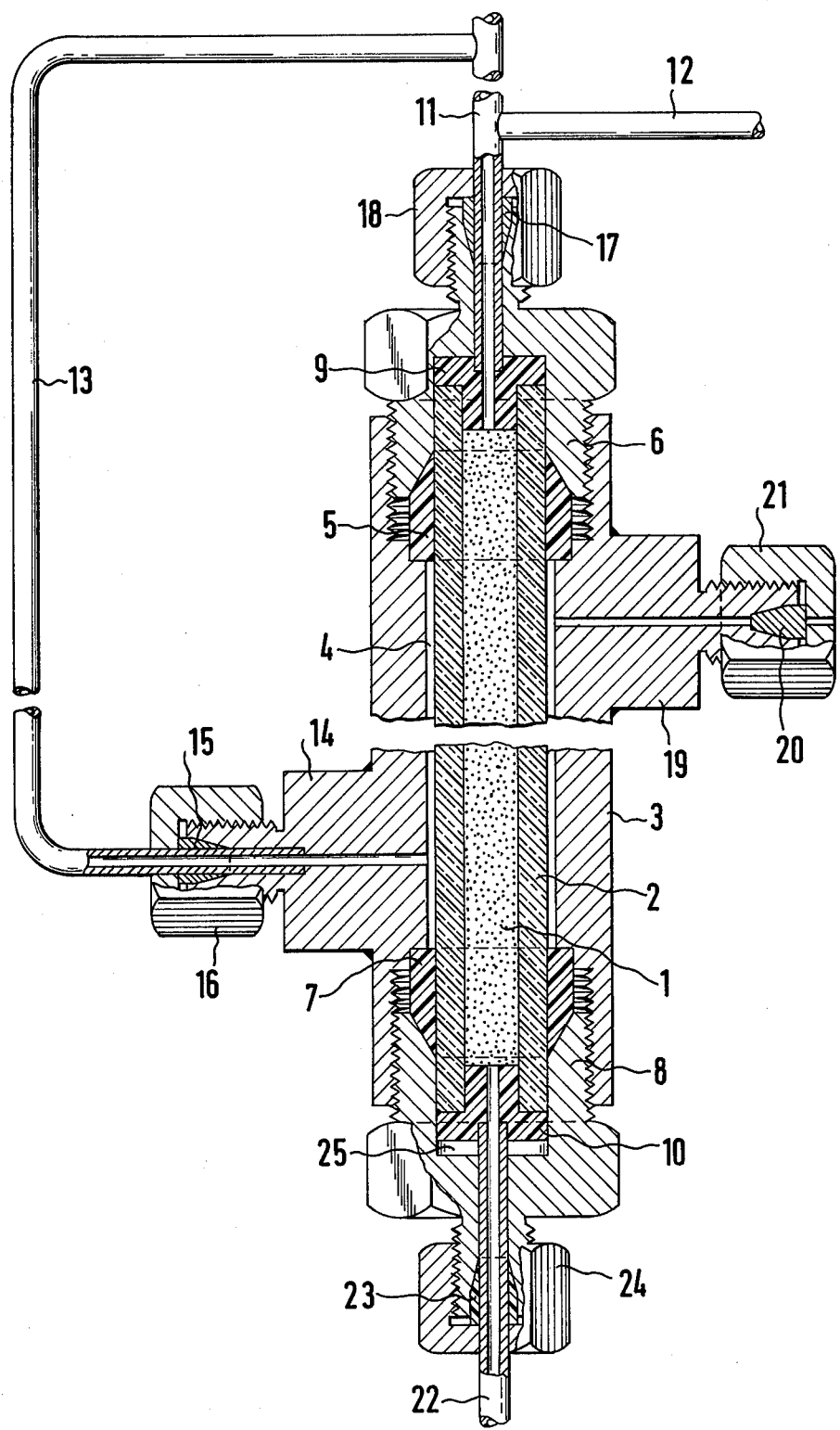

COLUMN FOR HIGH PRESSURE LIQUID CHROMATOGRAPHY

The invention relates to a column for high pressure liquid chromatography (HPLC) consisting of a glass column filled with sorbent concentrically surrounded by a pressure jacket leaving an interspace between the glass column and the pressure jacket, which interspace is sealed at both ends of the column and filled with the same medium as flows through the glass column, the pressure in the interspace being equal to the pressure at the inlet of the column.

German Utility Model No. 7,146,039 describes a separating column of this type in which the interspace between a steel column and a glass column is filled with a solvent, i.e. the medium flowing through the glass column, via a ring of porous material. At the lower end the interspace is sealed by a flat packing of an elastic material against which the lower end face of the glass column is pressed. When the column is put into service the gas in the interspace remains where it is and, owing to its compressibility, with pressure variations during chromatography (especially when the apparatus is set to work, working is discontinued and samples are introducd) a substance interchange between the point of sample feeding and the interspace takes place. When such substance interchanges are the reason for a loss of sample into the interspace these amounts of substance are eluated by the column at a later moment and possibly occasion separate peaks. By such memory effects a qualitative and quantitative analysis is adulterated. The substance interchanges may particularly result in disorders of the gradient profile with gradient elution.

German Offenlegungsschrift DOS No. 2,329,286 provides a separating column in which the aforesaid drawback is avoided by the fact that the interspace between the pressure jacket and the glass column is not in direct communication with the solvent inlet into the glass column and that the solvent is introduced into the interspace by a separate inlet. In this mode of construction the inlet side of the interspace must also be sealed with an elastic packing material against which the lower end face of the column is pressed. The disadvantage resides in the fact that the length of the glass column should be precisely adapted to the dimensions of the pressure jacket (maximum tolerance 0.2 mm) since under the high pressure to be considered of from 300 to 500 bars elastic O-rings cannot compensate higher tolerances and do not meet chromatographic demands with regard to chemistry.

The present invention provides a device with which the aforesaid disadvantages are avoided. This column for high pressure liquid chromatography (HPLC) consists of a glass column filled with sorbent and concentrically surrounded by a pressure jacket leaving an interspace between the glass column and the pressure jacket which interspace is sealed at both ends and filled with the same medium as flows through the glass column, the pressure in the interspace being equal to the pressure at the inlet of the column, wherein the interspace between the glass column and the pressure jacket is sealed by packings surrounding the glass column like stuffing boxes.

With an arrangement of this type deviations from the nominal length, adjusted to the pressure jacket, of the glass column of from 1 to 10 mm and more especially ± 1.5 mm, as occuring with products of different origin, are immaterial. Consequently, for sealing a relatively inelastic packing material can be used which has the advantage of a higher chemical resistance. Suitable packing material are, for example, those warranting a uniform pressure distribution on the glass column over a large surface area, such as different polymers of halofluorohydrocarbons, more especially polytetrafluoroethylene (PTFE) or low chlorinated PTFE (PCTFE). The packing material is pressed against the wall of the glass column by screwing, at both ends of the pressure jacket, sealing elements with outside threads like stuffing boxes. The packing material and the sealing elements are preferably of conical shape in order to compensate tolerances in diameter of the glass column and thus to ensure an especially good sealing effect. The sealing elements are provided with bores for the inlet and outlet of appropriate commercial reducing screw connections from 1/16 inch to ¼ inch. In a practical embodiment the inlet side can be constructed in such a manner that the sample feeding device of a commercial apparatus for high pressure liquid chromatography is directly used as stuffing box-like sealing element.

The interspace between the pressure jacket and the glass column is filled with solvent, i.e. the medium flowing through the glass column, via a separate pipe, while air or another gas present may escape through a vent tube preferably at the opposite end of the pressure jacket. After having closed the vent lock, a pressure builds up in the interspace corresponding to the pressure at which the medium is fed to the upper end of the glass column (300 to 500 bars). The same pressure acts from the outside on the lower end of the glass column while in the interior of the glass column a much smaller pressure prevails, for example 3 to 5 bars. By this pressure difference the glass column is not destroyed since a tubular structure has a higher resistance to a pressure acting from the outside, owing to known physical laws, than to an internal pressure. The height of the tolerance pressure is a function of the diameter, the wall thickness and the length of the column. The filling of the column (sorbent + mobile liquid phase) has an additional stabilizing effect.

After having let off the air from the interspace through the vent lock, air cushions cannot form so that no memory effects occur after pressure variations.

Owing to the fact that the interspace is sealed by pressing a sealing mass against the outer surface of the tube the position of the end face need not be defined within large tolerances, for example in the range of from 1 to 10 mm, especially ± 1.5 mm of nominal length of glass column. A possible tolerance volume is compensated by a glass capillary or a $V_4A$ capillary lined with PTFE in communication with the lower outlet of the glass column, which capillary may suitably be shiftable with respect to the sealing element.

A column for high pressure liquid chromatography having the aforesaid construction has important advantages. Its construction is simple without detrimental dead volumes and disturbing memory effects or other troubles occuring during operation. The solvent cannot dissolve any constituent of the packing and the simple construction ensures an easy manipulation. Owing to the simple construction and the resulting rapid exchangeability of the glass column, columns prepacked with sorbent, so-called prefabricated columns, especially columns with standardized separation effect, can be used. The column can be rapidly exchanged and installed in commercial HPLC apparatus. In such commercial apparatus it can be kept in a thermostat together with further equipment.

The invention will now be described with reference to the drawing illustrating by way of example a preferred embodiment of the column in longitudinal section.

Referring to the FIGURE, numeral 1 indicates the sorbent, 2 is the glass column, 3 the pressure jacket and 4 the interspace between the glass column and the pressure jacket.

Numeral 5 represents the packing surrounding the glass column at the inlet side. It is pressed against the wall of glass column 2 and against pressure jacket 3 by the screwed on sealing element 6. In the same manner the interspace 4 is sealed at the outlet side of the glass column 2 by packing 7 and sealing element 8. Packings 5 and 7 are made from polytetrafluoroethylene (PTFE). In the drawing the pressing surfaces of packings 5 and 7 and of sealing elements 6 and 8 are conical.

The glass column 2 is closed by two perforated stoppers 9 and 10 made of polytetrafluoroethylene which serve mechanically to confine the sorbent 1 to the column and to center capillaries 11 and 22. Capillary 11 having an outer diameter of 1/16 inch, passed through stopper 9, is used for the introduction of the solvent and the samples. Above the sample feeding tube 12 a pressure compensating capillary 13 is branched off from capillary 11 which is in communication with the interspace 4 by a short pipe 14 laterally welded on pressure jacket 3.

The pressure compensating capillary 13 is sealed with respect to short pipe 14 by a sealing cone of metal 15 and a union nut 16. In similar manner capillary 11 is sealed with respect to sealing element 6 by a sealing cone 17 and union nut 18. At the upper end of the pressure jacket 3, on the side opposite to the short pipe 14, a vent pipe 19 is welded which is sealed by a perforated closing cap 21 via a dummy seal 20. When the column is in operation the interspace 4 can be vented or its pressure released and flushed in a few seconds.

Lower stopper 10 is also perforated and bears capillary 22 which can be shifted with respect to sealing element 8 by a coneshaped packing 23 and union nut 24. Packing 23 may be made of polytetrafluoroethylene.

A tolerance volume between stopper 10 and sealing element 8 serves to compensate differences in length between the glass column 2 and pressure jacket 3. The tolerance volume 25 is bridged by discharge capillary 22 and thus cannot have an adverse effect on the chromatographic measurement.

Sealing elements 6 and 8 may have opposed threads, i.e. one a lefthand thread and the other one a righthand thread.

What is claimed is:

1. A column for high pressure liquid chromatography (HPLC) having a tube with an inlet and an outlet end and being filled with sorbent, said tube being concentrically surrounded by a pressure jacket so that an interspace between said tube and said pressure jacket is provided, which interspace is filled with the same medium as flows through the internal tube and the pressure in the interspace being equal to the pressure at the inlet of said tube, both ends of said interspace being sealed by means of packings surrounding said tube like stuffing boxes and sealing the interspace between said tube and said pressure jacket, and the interspace is connected by means of a pipe with the inlet end of said tube, a venting means is connected to the interspace, the pipe connected to the interspace opens up in a short pipe, the venting means is disposed on another short pipe mounted on the pressure jacket, and the two short pipes being mounted at opposite ends of the pressure jacket.

2. A column as claimed in claim 1, wherein the packings sealing the interspace between the glass column and the pressure jacket are made of polytetrafluoroethylene.

3. A column as claimed in claim 1, wherein a difference in length between the pressure jacket and the glass column is compensated by a discharge capillary capable of being shifted.

4. A column as claimed in claim 1, wherein an axially perforated stopper is inserted within each end of the tube, a capillary tube is inserted into the perforation in each of the stoppers, and each of the stoppers having a cylindrical shaft inserted within the tube.

* * * * *